(12) United States Patent
Farmer et al.

(10) Patent No.: US 6,613,036 B1
(45) Date of Patent: Sep. 2, 2003

(54) LIGHT-PROTECTIVE CONTAINER ASSEMBLY AND METHOD OF MAKING SAME

(75) Inventors: Randall M. Farmer, Mundelein, IL (US); Marc M. Daniels, Grayslake, IL (US); Lysander R. Garcia, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/496,066

(22) Filed: Feb. 1, 2000

(51) Int. Cl.[7] .................. A61B 19/00; A61L 15/00; B65D 75/00; B65D 33/16
(52) U.S. Cl. .................. 604/408; 604/403; 604/410; 604/415; 206/438; 206/828; 383/67; 383/113
(58) Field of Search .................. 604/403, 407, 604/408–410, 415; 206/461, 466, 471, 775–78, 828, 438, 262, 484.1, 1.5, 0.5, 524.1, 524.6; 383/38–40, 42, 61.1, 61.5, 67, 78, 62, 82–83, 86, 105, 106, 113, 115, 127

(56) References Cited

U.S. PATENT DOCUMENTS

| | | |
|---|---|---|
| 4,150,744 A | 4/1979 | Fennimore |
| 4,410,026 A | 10/1983 | Boggs et al. |
| 4,509,197 A | 4/1985 | Long |
| 4,548,605 A | 10/1985 | Iwamoto et al. |
| 4,557,959 A | 12/1985 | Kuehlein et al. |
| 4,700,838 A | 10/1987 | Falciani et al. |
| 4,998,400 A | 3/1991 | Suzuki et al. |
| 5,009,518 A | 4/1991 | Faltynek |
| 5,066,290 A | 11/1991 | Measells et al. |
| 5,364,384 A | 11/1994 | Grabenkort et al. |
| 5,489,022 A | 2/1996 | Baker |
| 5,520,972 A | 5/1996 | Ezaki et al. |
| 5,896,989 A | 4/1999 | Ropiak et al. |
| 6,039,718 A * | 3/2000 | Niedospial, Jr. |

FOREIGN PATENT DOCUMENTS

| | | |
|---|---|---|
| EP | 0 105 330 | * 10/1983 |
| EP | 0105330 | 4/1984 |
| EP | 0825223 | 2/1998 |
| FR | 2109147 | 5/1972 |
| JP | 08193149 | 7/1996 |

* cited by examiner

Primary Examiner—Angela D. Sykes
Assistant Examiner—Patricia Bianco
(74) Attorney, Agent, or Firm—Beth A. Vrioni

(57) ABSTRACT

Light-protective container assembly for a light-sensitive fluid includes a translucent container defining an inner reservoir to contain the fluid, and a flexible sleeve connected to the container. The sleeve has a tubular configuration sized to substantially cover at least the reservoir of the container, and is made of a material capable of substantially preventing the transmission therethrough of an identified range of wavelengths from the electromagnetic spectrum. Preferably, the sleeve is made of a mixture of a base material and a colorant capable of substantially preventing the transmission of undesired energy through a predetermined thickness of the base. material. The sleeve is connected indirectly to the container by providing the container with at least one passageway therethrough, and by positioning the sleeve such that a first portion of the sleeve is on one side of the container, and a second portion is on an opposite side of the container. The first and second portions are attached together through the passageway by a heat stake or fastener or the like. Preferably, the container is a flexible intravenous supply bag having a port structure at one end. A method of making the light-protective container assembly is also provided.

12 Claims, 4 Drawing Sheets

LIGHT-PROTECTIVE CONTAINER ASSEMBLY AND METHOD OF MAKING SAME

BACKGROUND OF THE INVENTION

1. Field of the Invention

The present invention relates to a light-protective container assembly for a light-sensitive fluid and, particularly, is directed to an intravenous flexible bag having a light-protective sleeve connected thereto so as to inhibit or prevent degradation of a light-sensitive solution contained within the flexible bag.

2. Description of Related Art

A variety of fluids are sensitive to at least a certain amount of electromagnetic energy within certain wavelengths, such as within the spectrum of visible light. Upon extended exposure, these fluids, hereinafter referred to generally as light-sensitive fluids, are susceptible to a chemical or photochemical reaction often resulting in degradation of the fluid. Depending upon the fluid, such reactions can take place within a matter of minutes or hours, while other fluids may require days or weeks before such degradation occurs. Light-sensitive fluids can be protected against such reactions by using a container made of a suitable material capable of blocking the transmission of detrimental electromagnetic energy. For example, the use of an opaque material is often preferred to protect against visible light. Certain situations or applications, however, preclude the use of opaque materials because visual inspection of the fluid is required. One such situation involves the use of intravenous or I.V. systems.

Flexible Intravenous (I.V.) bags are commonly used to store and administer medical agents to patients. The I.V. bags can contain a variety of fluids, such as water or saline, containing therapeutic agents including nutritional supplements, diagnostic substances, therapeutic substances, pharmaceuticals, medicaments and other drugs. A problem with such agents is that many are sensitive to electromagnetic energy, and particularly to light. Exposing such agents to light may cause a chemical or photo-chemical response, which often results in a loss of paternity and other undesirable impurities. Depending on the agent, this degradation can occur within 20 minutes of exposure to light or the like.

Furthermore, I.V. bags are typically flexible and made from a translucent or see-through material to allow visual inspection. In use, a caregiver hangs the I.V. bag on a pole. A delivery tube extends from the bottom of the bag to a needle that is inserted into the patient. The agent then gradually flows into the patient's body, usually over a 1- to 24-hour period. As such, the contents of the I.V. bag, as well as the I.V. bag itself, is potentially exposed to damaging amounts of light.

One way to prevent exposure of an agent to light would be to make the I.V. bag of an opaque material. However, there is a risk that the pigment or dye that constitutes the opaque material will leach from the bag and contaminate the fluid. This risk is especially significant if the agent in the I.V. bag is expected to have a long shelf life. Additionally, making the bag opaque prevents visual inspection of its contents. Visual inspection of the bag is beneficial both during the manufacturing process and during use to ensure that the fluid in the I.V. bag is clean and free of particulates and precipitates, and to verify the amount of fluid remaining within the reservoir.

Another way to prevent exposure of an agent to light is to enclose the I.V. bag in a sealed overwrap that is opaque. However, these overwraps generally are configured to be torn off and discarded when the I.V. bag is to be used. Thus, the bag and its contents are exposed to light during use.

To protect the fluid from light or similar electromagnetic energy, caregivers may cover the I.V. bag with a separate cover that is made of translucent material such as that available from Medipak of Winchester, VA. The use of such separate cover, however, involves an additional step in the administration of an agent. That is, when the overwrap has been torn from the I.V. bag, the translucent cover, if provided, must be removed from the overwrap and manually placed in proper position over the I.V. bag prior to administration. However, caregivers tend to use such separate covers inconsistently, while more often, the cover is merely discarded with the overwrap and not used at all. This failure can be detrimental to some fluids, especially those containing agents that react quickly to electromagnetic energy, such as light. Additionally, such covers generally are configured such that one size is intended to fit all applications. As a result, such covers tend to be ill fitting and allow ambient light to pass onto the I.V. bag.

Alternatively, caregivers may merely attempt to cover the I.V. bag with a towel, linen, or some other shroud. These make-shift shrouds commonly fail to completely shield the I.V. bag from light and often fall from the I.V. bag. Another problem is that these attempts to shroud the I.V. bag do not easily permit visual inspection of the I.V. bag and its contents. Typically, the caregiver must remove the shroud from the I.V. bag, which again exposes the agent to potentially harmful light. Each time that a caregiver removes such a cover or shroud, there is an increased likelihood that the I.V. bag will not be properly recovered and the agent will be exposed to damaging light. As such there remains a need for an improved light-protective container assembly, as well as a method of making the same.

SUMMARY OF THE INVENTION

The purpose and advantages of the present invention will be set forth in and apparent from the description that follows, as well as will be learned by practice of the invention. Additional advantages of the invention will be realized and attained by the methods and systems particularly pointed out in the written description and claims hereof, as well as from the appended drawings.

To achieve these and other advantages and in accordance with the purpose of the invention, as embodied and broadly described, the invention includes a light-protective container assembly for a light-sensitive fluid. The container assembly generally includes a translucent container, although more preferably transparent, and a flexible sleeve connected to the container. The container has an inner reservoir defined therein to contain the fluid. The sleeve, which is configured to substantially cover the container, is made of a material capable of substantially preventing the transmission of an identified range of wavelengths from the electromagnetic spectrum.

To connect the sleeve, the container preferably has at least one passageway defined therethrough, wherein the passageway is isolated from the inner reservoir. The sleeve has a first portion, which is positioned on one side of the container, and a second portion, which is positioned on an opposite side of the container. The first portion of the sleeve is attached to the second portion through the passageway to connect indirectly the sleeve to the container. Preferably, a plurality of passageways are provided, with the first and second portions of the sleeve being attached to each other through each passageway. Although a separate fastener, such as a snap, button, clip or adhesive, may be used, a heat stake or similar thermal weld is preferred.

The container is translucent, and more preferably transparent, to allow visual inspection selectively of the fluid contained therein and, in accordance with one aspect of the invention, the container is a flexible intravenous supply bag having a port structure at one end. As such, the sleeve is configured to extend at least over the reservoir of the container, and preferably over the port structure. Furthermore, and in accordance with a preferred embodiment, the first portion of the sleeve is a first side wall having opposite lateral edge portions, and the second portion of the sleeve is a second side wall having opposite lateral edge portions. In this manner, the lateral edge portions of the first side wall are integral with the lateral edge portions of the second side wall to define a tubular structure having at least one opened end to allow the sleeve to be displaced selectively for visual inspection of the container and the contents therein.

The sleeve is provided to prevent the transmission of electromagnetic energy having wavelengths that would be detrimental to the fluid to be contained within the container. Preferably, the identified range of wavelengths blocked by the sleeve is between about 190 nanometers to about 490 nanometers, and more preferably, the transmission is prevented of at least about 95% of the electromagnetic energy having wavelengths between about 290 nanometers to about 450 nanometers.

The present invention also includes a method of making a light-protective container assembly for a light-sensitive fluid. The method includes the step of identifying a range of wavelengths of the electromagnetic spectrum to which the light-sensitive fluid is susceptible to degradation. A translucent container having an inner reservoir therein, such as an intravenous bag, is provided to contain the light-sensitive fluid. The method further includes the steps of producing a flexible sleeve made of a material capable of substantially preventing the transmission of the identified range of wavelengths of the electromagnetic spectrum, wherein the sleeve is configured to cover the container, and then connecting the sleeve to the container.

To produce the sleeve, the method preferably includes preparing a mixture of a base material for the sleeve and a colorant capable of substantially preventing the transmission of the identified range of wavelengths of the electromagnetic spectrum through a predetermined thickness of the base material. For example, and with regard to the sleeve embodied herein, a pigment formulation is used including a sufficient amount of yellow pigment formulated 5 to prevent the transmission of at least about 95% of electromagnetic energy having a wavelength between about 290 nanometers to about 450 nanometers through the predetermined thickness of the base material. The mixture is then formed into the sleeve, preferably so as to have a tubular configuration with side walls of the predetermined thickness.

In a preferred embodiment, the sleeve is connected indirectly to the container by including at least one passageway through the container, wherein the passageway is isolated from the inner reservoir. The sleeve is positioned on the container with one portion of the sleeve on one side of the container and another portion on an opposite side of the container. The first and second portions are then attached together, such as by a heat stake or a fastener, through the passageway to connect indirectly the sleeve to the container.

It is to be understood that both the foregoing general description and the following detailed description are exemplary and are intended to provide further explanation of the invention claimed.

The accompanying drawings, which are incorporated in and constitute part of this specification, are included to illustrate and provide a further understanding of the method and system of the invention. Together with the description, the drawing serves to explain the principles of the invention.

DETAILED DESCRIPTION OF THE PREFERRED EMBODIMENT

Reference will now be made in detail to the present preferred embodiment of the invention, an example of which is illustrated in the accompanying drawing. The method and corresponding steps for the manufacture and use of the invention will be described in conjunction with the detailed description of the assembly.

Figure 1:
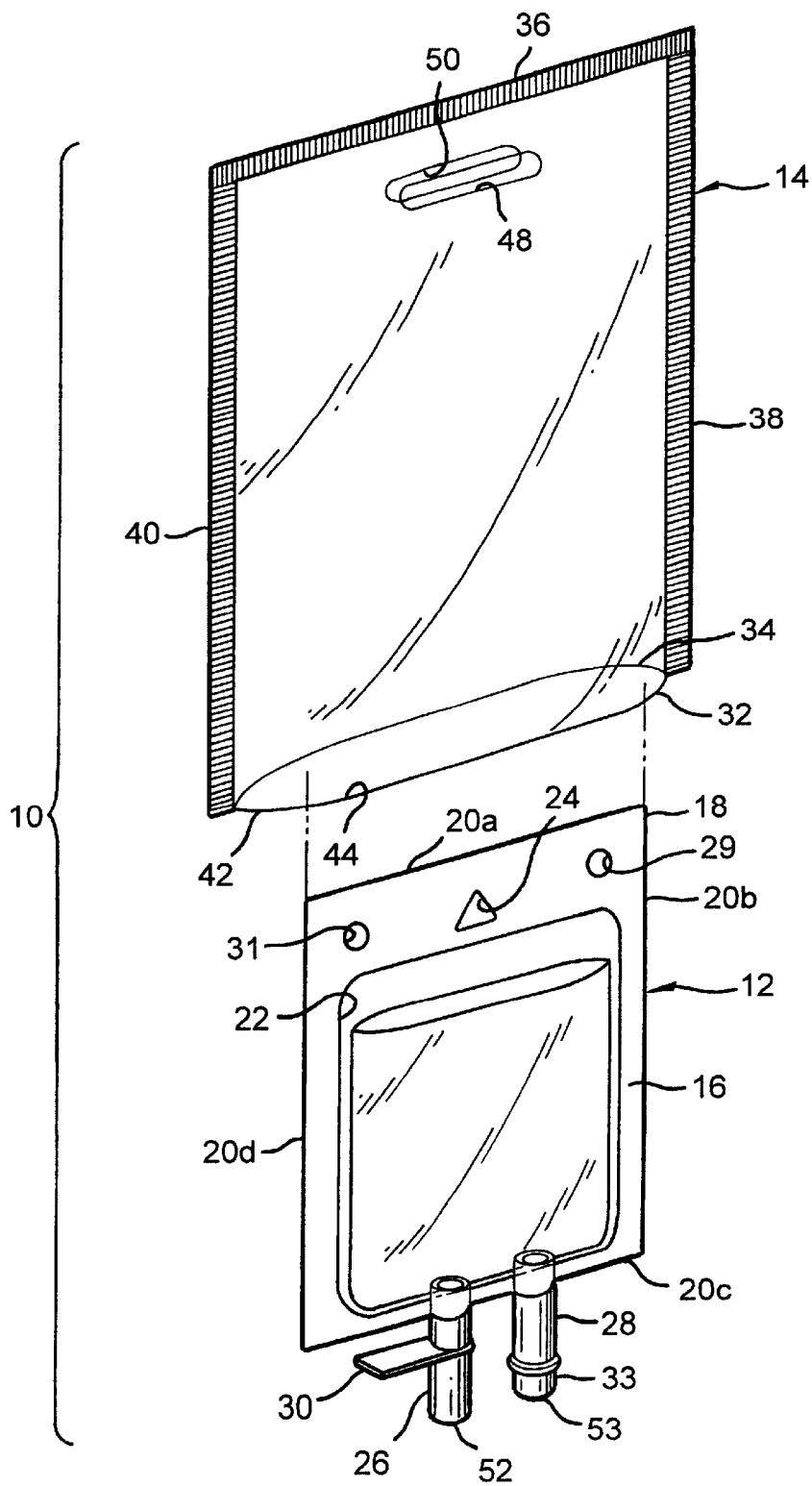
FIG. 1 is an exploded front perspective view of one representative embodiment of a light-protective container assembly of the present invention.

The assembly presented herein may be used for the storage, shipment and delivery of a variety of light-sensitive fluids. The assembly of the present invention is particularly suited for use in the intravenous delivery of a light-sensitive solution comprising a base fluid and a light-sensitive agent. For purpose of explanation and illustration, and not limitation, an exemplary embodiment of the system in accordance with the invention is shown in FIG. 1 and is designated generally by reference character 10.

The light-protective container assembly in accordance with the present invention includes the combination of a translucent container defining an inner reservoir suitable to contain the light-sensitive fluid, and a flexible sleeve connected to the container. As described in greater detail below, the sleeve of the present invention is configured to substantially cover the container, and is made of a material capable of substantially preventing the transmission of an identified range of wavelengths of the electromagnetic spectrum.

Any of a variety of container configurations may be used in accordance with the present invention. For example, and as embodied herein, the container may be a substantially conventional flexible bag 12 used for intravenous (I.V.) applications and delivery. Such flexible bags are well known, and can be formed using a variety of construction techniques. FIG. 1 shows an I.V. or primary bag 12 formed of two sheets or layers 16 and 18 of translucent material bonded together at their perimeter to form flanges 20a–20d and to define a reservoir 22 therein. Preferably, although not necessarily, the translucent material is transparent for enhanced visual inspection of the container and its contents.

Additionally, the container may have a port structure for fluid communication with the reservoir of the container. FIG. 1 shows the port structure of the flexible bag container 12 embodied herein being defined by one or more tubular members 26 and 28 located proximate the bottom of the container. The first tubular member 26 includes a conventional fitting adapted for connection to a delivery set (not shown) for delivery of fluid from the reservoir. A second tubular member 28 is provided to define a port, preferably covered by a septum 33 or similar valve configuration, to allow the introduction of an additive or agent into the reservoir 22. An overcap having a flange 30 can be provided on the first tubular member 26, to enhance gripping by the caregiver for removal of the overcap 30 for connection of the first tublar member 26 to a delivery set.

Preferably, the container also includes a mounting structure to receive or otherwise engage a support structure if desired during use and operation of the container. For example, and with reference to the flexible bag of FIG. 1, a hanger hole 24 may be defined through the top flange 20a to permit the bag container 12 to be hung on the hook of an I.V. pole as shown schematically in FIGS. 5A and 5B. Alternative structures likewise can be used.

The primary bag container 12 preferably is formed of a substantially clear and flexible material, such as, but not limited to, PVC, polyester, polypropylene, or the like. By being translucent, and preferably transparent, the primary bag container 12 and its contents are capable of visual inspection, which can be important during manufacture and storage of the container and the administration of the desired fluid contained therein to a patient. Such inspection permits the manufacturer or caregiver to inspect the container 12 and its contents, and to ensure that the fluid in the reservoir 22 is free of any undesired particulate or precipitate that may form during manufacture and storage. Such inspection also is important when additives or agents are stored within the container 12, or introduced into a base fluid initially stored within the reservoir 22, as described further below.

The flexible bag container 12 embodied herein may be used to store and deliver a variety of fluids, preferably including one or more therapeutic agents such as drugs, medicaments, nutritional supplements, and diagnostic agents, either alone or mixed with a base fluid. For example, the agent can be in the form of a solution, a suspension, a biological fluid, or any other type of deliverable material. The therapeutic agent may be packaged and stored initially in the flexible bag container or, as in the preferred embodiment, the agent can be introduced when needed via the tubular member 28 into a base fluid initially contained within the flexible bag container 12. Often, however, this therapeutic agent is sensitive to at least some portion of the electromagnetic spectrum, particularly light from the visible and/or invisible portions of the spectrum. In accordance with the present invention, the method of making the light-protective container assembly includes identifying the range of wavelengths of the electromagnetic spectrum to which this light-sensitive fluid is susceptible to degradation. A variety of known techniques may be used to identify this susceptible wavelength range for the contents of the container, including but not limited to known experimental and analytical techniques.

As noted above, and in accordance with the present invention, the light-protective container assembly further includes a sleeve connected to the container. A variety of sleeve constructions can be used, provided the sleeve is configured to substantially cover the container. That is, and as described further below, the sleeve is made of a material capable of substantially preventing the transmission of an identified range of wavelengths of the electromagnetic spectrum, and is sized and shaped so as to substantially shroud at least the reservoir of the container to prevent such transmission thereto.

For example, but not by limitation, the sleeve 14 embodied herein for the flexible bag container 12 is formed of a first side wall 32 and a second side wall 34, each having opposite lateral edge portions 38, 40. Preferably, the lateral edge portions of the first side wall 32 are formed integral with the lateral edge portions of the second side wall 34 to define a tubular structure. The first and second side walls 32, 34 therefore can be formed separately and then bonded or sealed together to define the tubular structure; or the first and second side walls 32, 34 can be formed of a single sheet that is folded over and then bonded or sealed along the edge portion opposite the fold to define the tubular structure; or the first and second side walls can be extruded together as a single element defining the tubular structure.

FIG. 1 shows the first and second side walls 32 and 34 bonded or sealed together along the upper edge portion 36 of the tubular structure, as well as along substantially the entire length of each lateral edge portion 38, 40. In this manner, the tubular structure has an opened lower end 42 to allow the sleeve to be displaced relative the container 12 for visual inspection of the container 12 as described further with regard to FIG. 5B. It is possible, if desired, to bond or seal only a section of one or both lateral edge portions together, such as along an upper section thereof proximate the upper edge portion 36 of the tubular structure. In this manner, the remaining sections of the lateral edge portions 38, 40, as well as the lower edge portion 44 if desired, can be releasably adhered or attached together to allow separation of the first and second side walls 32, 34 along the releasable edge portions selectively for visual inspection of the container and then re-attached when visual inspection is completed. Furthermore, it is not necessary to seal the upper edge portion 36 of the tubular structure. If unsealed, however, the upper edge portion 36 preferably is provided with a flap or similar member (not shown) to prevent the transmission of undesired light or the like thereat.

The sleeve 14 embodied herein is positioned over the flexible bag container 12 such that the upper edge portion 36 of the tube structure is proximate the top of the container 12, and the opened lower end 42 of the tubular structure is proximate to and preferably extends beyond the first and second tubular members 26 and 28 defining the port structure of the container 12. This configuration inhibits the transmission of undesired light or electromagnetic energy into the container, yet allows relatively easy access to the first tubular member 26 for connection of a delivery set (not shown) and to the second tubular member 28 for the introduction of additives and agents into the reservoir 22. It is possible, however, for the sleeve 14 to be sized such that the lower edge portion 44 of the sleeve 14 is located between the bottom edge 20c of the primary bag 12 and the bottom edges 52 and 53 of the tubular members 26 and. 28 to provide even greater access to the ports defined by the first and second tubular members 26 and 28, yet still completely cover the reservoir 22 of the primary bag container 12.

Figure 3:
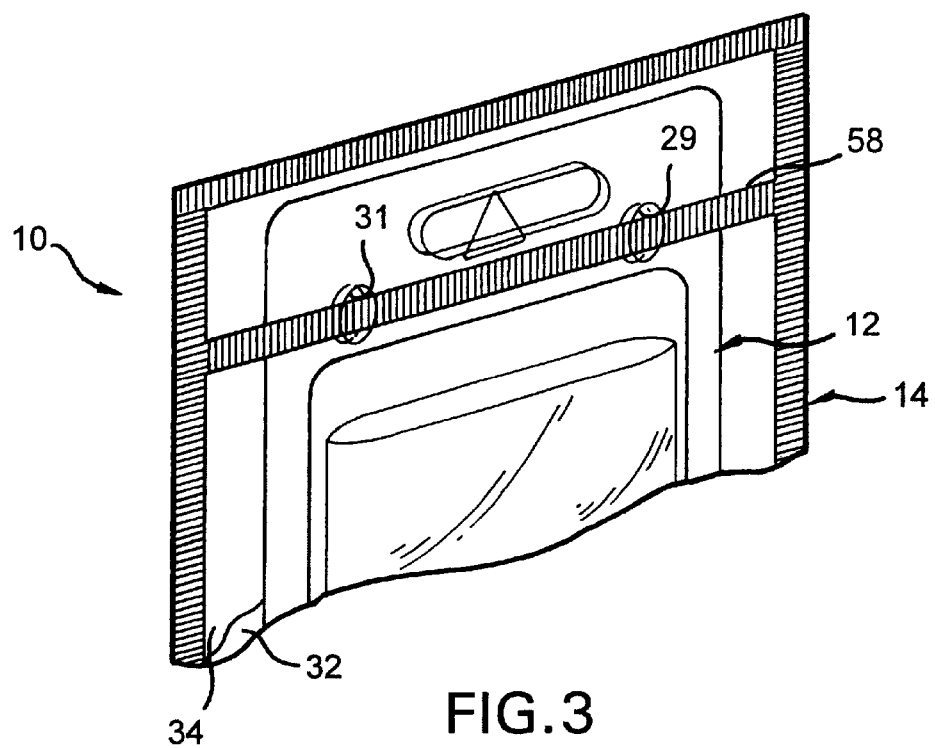
FIG. 3 is an enlarged partially-fragmented view an alternative connection between the sleeve and the container of the assembly shown in FIG. 1.
Figure 2:
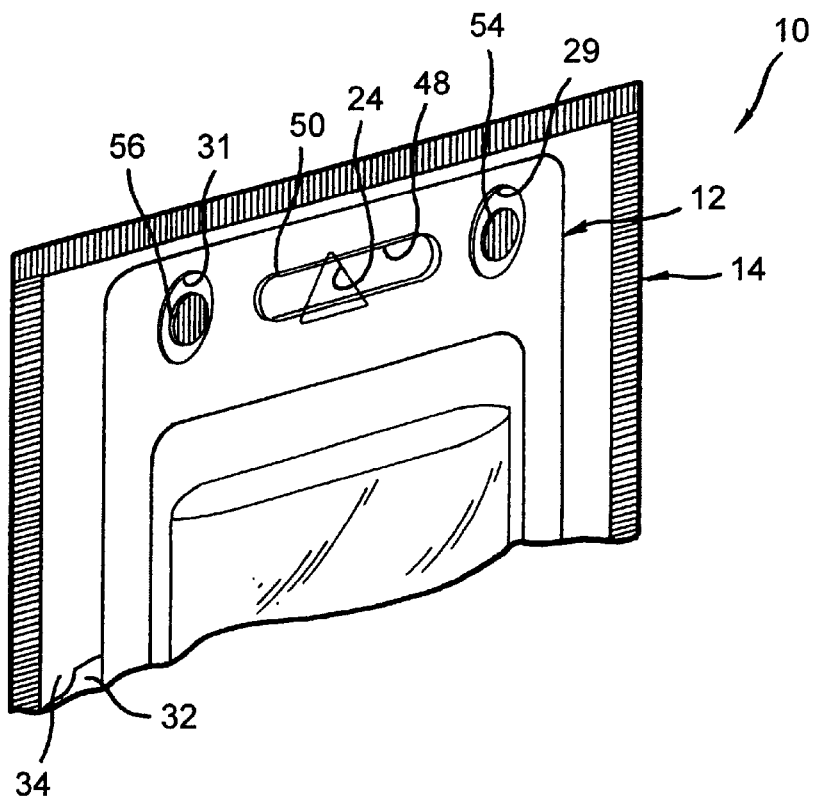
FIG. 2 is an enlarged partially-fragmented view showing a representative embodiment of the connection between the sleeve and the container of the assembly shown in FIG. 1.

As previously noted, the container preferably includes a mounting structure, such as opening 24 as shown in FIG. 1, to receive or engage a support structure. In accordance with another aspect of the invention, the sleeve 14 is provided with at least one corresponding opening therethrough for access to the mounting structure. FIGS. 1–3, for example, show an elongated opening 48 and 50 defined in the first side wall 32 and second side wall 34, respectively, of the sleeve 14 to allow a support structure, such as member 74 shown in FIGS. 5A and 5B, to be inserted therethrough and into engagement with mounting structure 24. These openings can be formed in the side walls 32, 34 by any punching, molding or other known process.

In accordance with the invention, the sleeve is made of a material capable of substantially preventing the transmission of an identified range of wavelengths of the electromagnetic spectrum. The identified range can correspond to visible and/or non-visible light, depending upon the range of wavelengths that are to be blocked. For example, and as previously noted, certain therapeutic agents are susceptible to degradation when exposed to electromagnetic energy within a certain range of wavelengths. In accordance with the method of the present invention, and also as previously noted, this range of wavelengths is first identified such that the sleeve is produced to prevent the transmission of at least this identified range.

The transmission of the undesired energy can be prevented, for example, by reflection, refraction, polarization, dispersion or absorption of the portion of the electromagnetic spectrum corresponding to the identified range. In this manner, the material used for the sleeve is substantially opaque to at least the identified range of wavelengths of the electromagnetic spectrum. Preferably, however, the sleeve also is suitably translucent to allow at least preliminary inspection of the container without requiring displacement of the sleeve. Such preliminary inspection should be suitable at least to identify large particulates within the reservoir, as well as possibly inspect the meniscus of the fluid contained therein. For example, and in a preferred embodiment, this opaqueness can be established by adding a colorant such as pigments, dye, ink or the like to a translucent, and preferably transparent, base material used for the sleeve. The colorant can be a single color, such as a yellow pigment, or it can incorporate a combination of different pigments if desired. The amount of colorant required will depend not only upon the type of colorant used, but also upon the type and thickness of the base material used.

In addition to the colorant, an agent can be added to the material to aid in disbursement of the colorant. For example, if pigment is used as the colorant, it may be necessary or beneficial to add an appropriate amount of wax or similar agent and/or a material similar to the base material but ground or formed into flakes to assist in dispersion of the pigment within the base material as is known in the related art. Additional substances or compounds can be added to provide protection for both the sleeve and the contents of the container against non-visible light, as well as to enhance the performance characteristics of the sleeve itself. If desired, the sleeve also can be provided with a matte finish to further reduce the transmission of undesired energy by dispersion or the like of undesired electromagnetic energy.

A variety of different materials can be used to form the sleeve. A preferred embodiment, as noted above, includes the combination or mixture of a base material for the sleeve and a colorant, such as a pigment formulation, capable of substantially preventing the transmission of the identified range of wavelengths of the electromagnetic spectrum through a predetermined thickness of the base material. This mixture is then formed into the sleeve material so as to have one or more walls of the predetermined thickness.

For example, but not by limitation, it was determined through experimental process that a certain light-sensitive fluid to be delivered by a flexible bag container was susceptible to degradation when exposed to electromagnetic energy having a wavelength identified in the range of about 290 nanometer to about 450 nanometer, and particularly in the range of about 410 nanometer to 450 nanometer. A sleeve was therefore desired to prevent, substantially, the transmission of electromagnetic energy having a wavelength identified between about 290 nanometers to about 450 nanometers and, particularly, between about 410 nanometers to about 450 nanometers. To ensure flexibility of the sleeve, it was desired to maintain the thickness of the material used for fabrication of this exemplary sleeve between about 0.051 mm (2.0 mils) to about 0.061 mm (2.4 mils), and preferably with a predetermined thickness of about 0.056 mm (2.2 mils).

In this exemplary embodiment, a sheet was extruded using a chill roll from a blend of Exxon PD9012E1 polypropylene, 8.5% PP7200P polypropylene flake, 1% Acrawax C, and 3% Chromophthal Yellow GR, so as to have a 55 RA matte finish. This blend is commercially available from Chroma Corporation of McHenry, Ill. Exxon PD9012E1 is a polypropylene random copolymer having 3% ethylene. Other examples of materials that can be used to form the sleeve include PVC, polyolefins, and high-density polyethylene. Chromophthal Yellow GR is an azo condensation organic pigment that has the chemical name benzamide, 3,3'-{(2,5-dimethyl-1,4-phenylene)bis{imino(1-acetyl-2-oxo-2,1-ethanediyl)azo}}bis{4-chloro-N-(5-chloro-2-methylphenyl)-. Amoco PP7200P is a polypropylene homopolymer, and Acrawax C is an ethylene is a stearamide wax. Exxon PD9012E1 is commercially available from Exxon Chemical Americas of Houston, Tex. Chromophthal Yellow GR is commercially available from Ciba Specialty Chemicals Corporation of Newport, Del. Amoco PP7200P is commercially available from BP Amoco of Chicago, Ill., and Acrawax C is commercially available from Lonza LTD. of Basel, Switzerland. Particularly, and for purpose of illustration, the sleeve material was first cast extruded into a sheet having a thickness of about 0.056 millimeters using a chill roll with a matte finish so as to provide a matte finish to the film. Sheets from two rolls of extruded material were layered and the appropriate edge portions were heated to form a heat seal to secure the sheets together and form a continuous web of sleeves. The sleeves were then separated to form sleeves 14 each with the desired length of 265.1 millimeters and width of 133.4 millimeters. The sleeve's dimensions enable it to provide light protection to a flexible bag container similar to the 250 ml I.V. bag container sold by Abbott Laboratories of Illinois, and its material of construction allows autoclaving up to 125° C.

Figure 6:
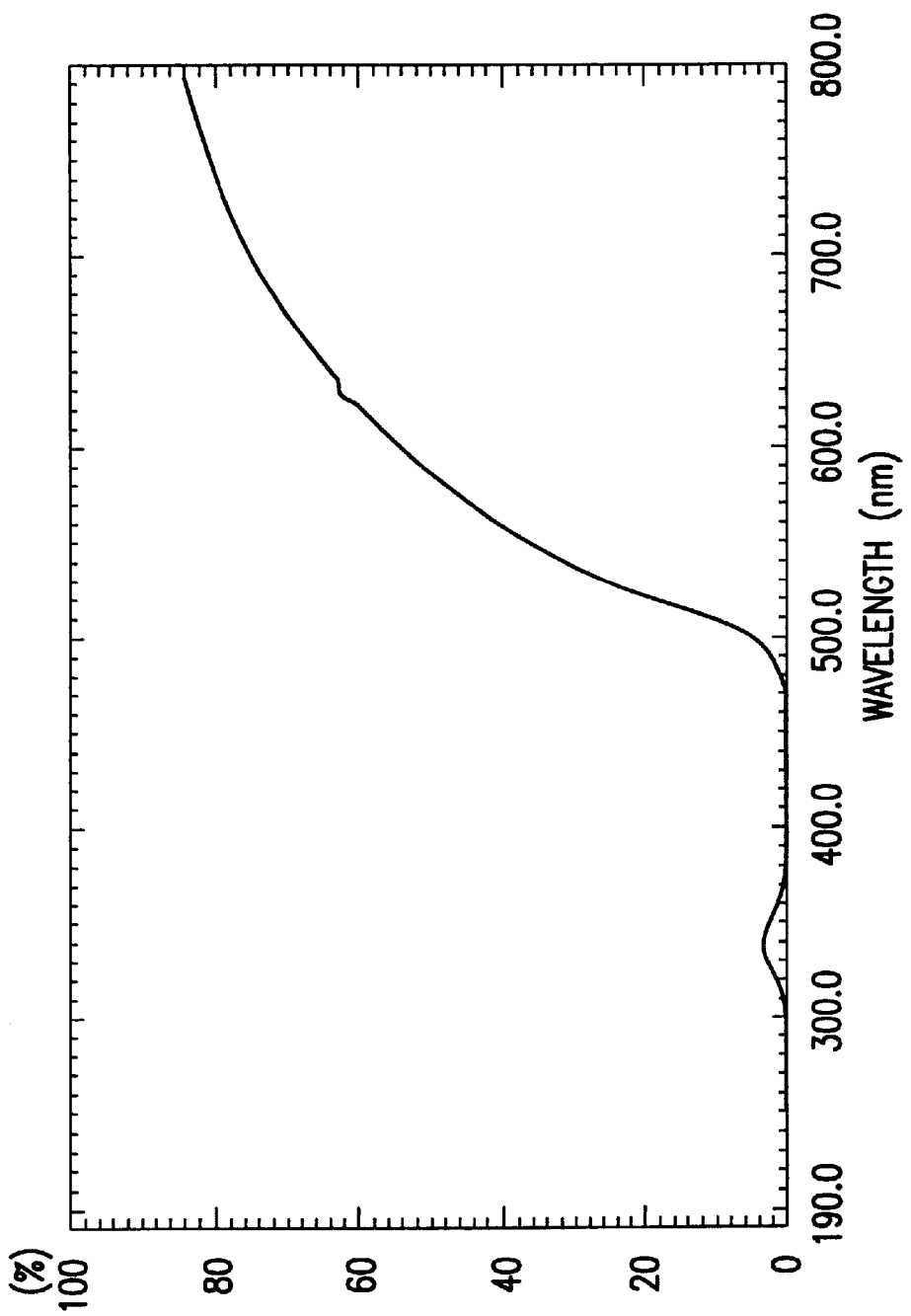
FIG. 6 is a graphical representation of light transmission measured as a function of wavelength for the exemplary embodiment of the present invention.

The resulting summed light transmission of electromagnetic energy for this exemplary embodiment was determined by measuring the percent of light transmitted through the film at ten nanometer increments. For example, a plot of measured light transmission as a function of wavelength is shown graphically in FIG. 6. As such, and for the 410 to 450 nanometer range, the percent of light transmitted was summed for the wavelengths of 410, 420, 430, 440, and 450 nanometers. The summed transmission of light for this exemplary embodiment is set forth in Table 1.

TABLE 1

| | Summed Light Transmission, % | | |
|---|---|---|---|
| Film Thickness | | 410–450 nm | 290–450 nm |
| Average | 2.20 | 0.23 | 2.87 |
| Range | 2.06–2.54 | 0.13–0.40 | 1.29–4.86 |

The relationship between summed light transmission, film thickness, and pigment concentration can be defined according to the following equation:

$$\ln(\text{light\_transmission}) = A \times (\text{pig\_conc} \times \text{film\_thickness}) + B$$

where "light_transmission" is the summed percent of light transmission, "pig_conc" is the percent of pigment concentration in the film, "film_thickness" is the thickness of the film in millimeters, and "A" and "B" are constants calculated by regression analysis of a plot of ln(light transmission) versus (pigment conc x film thickness). For film that is substantially opaque in the 410 to 450 nanometer range and has a 55 RA matte finish, it has been determined that A=−0.6464 and B=2.9068. For film that is substantially opaque in the 290 to 450 nanometer range and has a 55 RA matte finish, A=−0.6253 and B=5.4169. For film that is substantially opaque in the 410 to 450 nanometer range and does not have a matte finish, A=−0.9017 and B=7.0963. For film that is substantially opaque in the 290 to 450 nanometer range and does not has a matte finish, A=−0.6603 and B=6.0073.

Although one exemplary embodiment is provided, the construction and characteristics of the sleeve can be modified accordingly to prevent the transmission of alternative portions of the electromagnetic spectrum, and yet maintain flexibility and toughness, such as by altering the material of construction, the resulting thickness, and/or the pigment formulation and concentration. Indeed, and if desired, the sleeve can be fabricated using an appropriate material, or pigment formulation, that is opaque to substantially all energy having a wavelength below 800 nanometers, or a defined portion thereof, such as within any desired range defined between about 10 nanometers to about 800 nanometers.

The acceptable amount of energy transmission that is to be prevented will depend upon the sensitivity of the fluid to be protected. Generally, however, it is preferred that the sleeve prevent sufficient transmission so as to result in a summed percent of light transmission for a given range that is at least below about 40%, although a summed percent of light transmission below about 10% is more preferred, and a summed percent of light transmission below about 5 % is particularly preferred for more sensitive fluids, such that at least about 95% of the electromagnetic energy in the identified range is blocked. Additionally, although a relationship between known parameters and summed percent of light transmission are presented above for one embodiment, a different relationship between the summed percent of light transmission, concentration of pigment, and film thickness of the sleeve can be expected for alternative embodiments, particularly if the sleeve material embodies a more complex pigment formulation of two or more colors.

A variety of techniques are known and can be used for connecting the sleeve to the container. In accordance with an additional aspect of the present invention, however, the sleeve and the container are not connected directly together. That is, it is preferred that direct communication is not provided between the material of the sleeve and that of the container. In this manner, leaching of pigments or similar elements from the sleeve to the fluid within the container can at least be inhibited. FIG. 1 shows, for example, one or more passageways 29 and 31 defined through the flexible bag container 12. The passageways 29, 31 are formed, such as by punching, molding or any other known technique, through the top flange 20a so as to be isolated from the inner reservoir 22 of the container 12. If desired, one or more such passageways can be located elsewhere on the container, in addition to or instead of through the top flange 20a. If an alternative type of container is used, such as a bottle or vial, a similarly-suitable passageway can be provided to allow the sleeve to be connected indirectly thereto.

To connect the sleeve to the container, a first portion of the sleeve is positioned on one side of the container proximate the passageway, and a second portion of the sleeve is positioned on an opposite side of the container proximate the passageway. The first and second portions of the sleeve thus can be attached together through the passageway so as to connect indirectly the sleeve to the container. For example, and with reference to FIG. 2, the sleeve 14 is positioned over the flexible bag 12 such that the first and second side walls 32, 34 are positioned on opposite sides of the flexible bag 12. In this preferred embodiment, the first and second side walls 32, 34 are attached to each other through each passageway 29, 31 formed through the top flange 20a of the container 12. Although a separate fastener, such as a snap, button, clip or adhesive, may be used to attach the opposing side walls together through each passageway, the preferred embodiment of FIG. 2 uses a heat stake or similar thermal weld. Particularly, FIG. 2 shows the first and second side walls 32, 34 attached together using first and second heat stakes 54 and 56 therebetween. These heat stakes 54, 56 are aligned with first and second passageways 29 and 31 formed in the top flange 20a of the primary bag 12. The heat stakes 54 and 56 are formed by applying thermal energy to the sleeve 14 in an isolated manner to adhere the opposing side walls 32 and 34 to one another through the passageways 29 and 31, without contacting the flexible bag container 12.

An alternative method of heat staking the opposing side walls 32, 34 together is shown in FIG. 3. In this embodiment, thermal energy is applied continuously across the sleeve proximate the region 58 wherein the passageways are located as shown in FIG. 3. This continuous application can be performed using a heated bar or the like. The applied thermal energy is controlled, however, to ensure that sufficient energy is applied to soften or partially melt the opposing side walls 32, 34 of the sleeve 12 without softening or melting the container 12. As such, the material used for fabrication of the container 12 in this embodiment preferably will have a higher melting temperature than that of the sleeve 14, and the applied thermal energy will be maintained between the two melting points. Once the side walls 32, 34 are sufficiently softened, the thermal energy is removed, preferably with compression maintained on the sleeve, such that the opposing side walls will adhere to one another through the passageways 29 and 31 of the flexible bag container 12 along heat stake region 58, without adhering to the container itself. Hence, the sleeve 14 is connected indirectly to the flexible bag 12 through the passageways 29 and 31.

As previously noted, it likewise is possible to connect the sleeve 14 to the bag 12 using a fastener (not shown), such as a self-piercing, snap-type fastener, which has a stud configured to engage a ring. For example, and with reference to FIG. 2, the stud would be aligned with a corresponding passageway 29, 31 in the flexible bag container 12 and pierced through the side walls 32, 34 of the sleeve 14 so as to be engaged by the opposing ring. This snap-type fastener also can be used to connect the sleeve 14 to a container that does not have passageways therein, particularly if the fastener is made of a material that would inhibit the transmission of pigments to prevent leaching. That is, and with reference to FIG. 1, the fastener could be provided to pierce through the top-flange 20a of the primary bag 12 at a point that does not compromise the integrity of the reservoir 22.

When the light-protective container assembly includes a flexible bag container, such as for I.V. applications, it is preferable to provide an overwrap element configured to encase the assembly of the flexible bag container and sleeve in a sealed environment. Preferably, and as embodied in FIG. 4, the overwrap element 60 is made of a material that is opaque to a substantially broad range of wavelengths, including substantially all visible and ultraviolet light. A preferred material of constructions includes a metal foil and plastic laminate such as polyester (PET)/foil/polypropylene (PP). Such overwrap elements are known and can be formed using a variety of different methods including multi-layer laminating techniques. Due to its construction, the overwrap element is particularly beneficial for shipping and storage of the light-protective container assembly as a whole. For example, the overwrap element provides security and strength for shipping and storage, added protection from light, and a vapor seal to inhibit evaporation and osmotic transfer to maintain the fluid levels within the primary bag container.

Until use of the container is desired, the overwrap element 60 thus is sealed along all edges to encase the connected combination of the container and sleeve therein. In accordance with another aspect of the present invention, the overwrap element may be provided with a translucent window 62 to allow visual inspection of the container and sleeve combination. For example, and when a suitable sleeve is connected to the container to prevent the transmission of the identified range of energy, the window can be made of a transparent material. Alternatively, the window 62, itself can be made of a material capable of substantially preventing the transmission of an identified range of wavelengths of the electromagnetic spectrum to further protect any light-sensitive fluid within the container 12. The polypropylene layer in the window 62 therefore can be produced in a manner similar to that previously described for the sleeve 14. The window 62 thus would be opaque to at least a portion of the light spectrum, but not opaque to all of the visible or ultraviolet light. Additionally, or alternatively, the window 62 can be provided with a cover or flap (not shown) made of opaque material to further protect against light transmission. Because the window 62 may affect the overall moisture transmission rate of the overwrap element 60, however, it is preferred that the window 62 be limited in size to reduce moisture transmission thereacross. For example, and with reference to the exemplary embodiment of the light-protective container assembly previously described, a window constructed of polyester/polypropylene preferably should have an overall surface area of no greater than 3⅛ in.$^2$ (20.2 cm$^2$) when provided with a total thickness of approximately 0.088 mm. The required window size however will be dependent on fill volume, assay, claimed shelf life and storage temperature.

Figure 4:
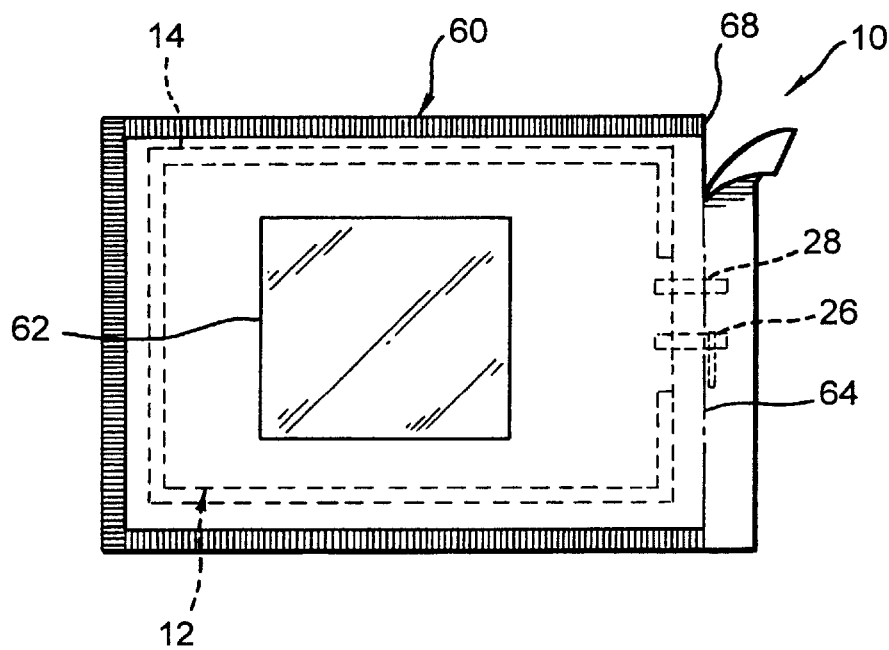
FIG. 4 is a front view of the light-protective container assembly shown in FIG. 1, as enclosed in an overwrap that is torn partially open.
Figures 5A, 5B:
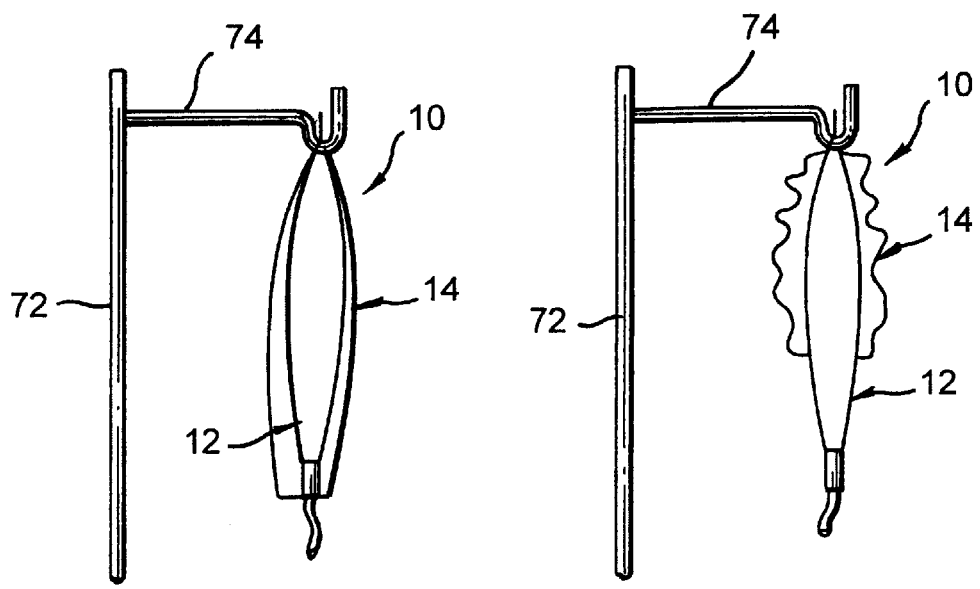
FIGS. 5A and 5B are schematic side views demonstrating a method of using the light-protective container assembly shown in FIG. 1.

For purpose of explanation and not limitation, reference is now made to the operation of the light-protective container assembly of FIG. 1, as shown schematically in FIGS. 4 and 5A–5B. That is, when used for purpose of I.V. applications, the overwrap element 60 is torn open such that the connected combination of the flexible bag container 12 and sleeve 14 can be readily removed as a single, integral unit. A notch 68 can be provided in the overwrap 60 to facilitate a tear generally along line 64 for removal of the container-sleeve combination. The overwrap element 60 then can be discarded. As may be necessary, one or more prescribed doses of agent thus can be injected through the port of the second tubular member 28 and mixed with the diluent base fluid stored in the primary bag container 12. As shown in FIG. 5A, and with the overwrap removed the container assembly 10 can be mounted on a support structure, such as an I.V. pole 72, so that the hanging hook 74 passes through the openings 48 and 50 of the sleeve 14 and the mounting structure 24 of the primary bag container 12.

As shown in FIG. 5A, the sleeve 14 is connected to cover the primary bag container 12 and prevent exposure of the agent to harmful wavelengths of electromagnetic energy. Generally, however, the haziness, thickness, and/or opaqueness of the sleeve 14 likewise may preclude adequate visual inspection of the container 12 through the sleeve 14. For example, the caregiver may be able to see through the sleeve 14 well enough to detect large particulates in the reservoir or to inspect the meniscus or volume of fluid therein, but cannot see enough detail to inspect whether the agent is adequately mixed in the diluent.

Because the lower end 42 of the sleeve 14 is open, the caregiver can visually inspect the contents of the bag container 12 simply by displacing the sleeve 14 relative to the container 12, such as in an upward manner as shown in FIG. 5B. Preferably, the sleeve 14 is configured and constructed to return to its initial position when released by the caregiver so as to cover the container 12. Visual inspection is not limited to when the container assembly 10 is mounted on the I.V. pole 72 as illustrated in FIGS. 5A and 5B. Indeed, visual inspection can be performed at any time as may be desired, such as during the manufacturing process or when mixing the agent before the I.V. bag assembly 10 is mounted on the pole 72. If the sleeve were sufficiently translucent, however, it is possible that the caregiver would be able to perform a preliminary inspection by viewing the contents of the primary bag 12 through the sleeve 14 such that the caregiver would not need to lift the sleeve 14 to expose the primary bag 12 to any additional electromagnetic energy.

Although one embodiment of the light protective container assembly and the method of making such a container assembly has been-described, many other configurations may be provided. Indeed, it will be apparent to those skilled in the art that various modifications and variations can be made in the method and system of the present invention without departing from the spirit or scope of the invention. Thus, it is intended that the present invention include modifications and variations that are within the scope of the appended claims and their equivalents.

What is claimed is:

1. A light-protective container assembly for a light sensitive fluid, the assembly comprising:

a translucent container defining an inner reservoir to contain a fluid; and a flexible sleeve connected to the container, the sleeve being made of a material capable of substantially preventing the transmission of an identified range of wavelengths of the electromagnetic spectrum, the sleeve being configured to substantially cover the reservoir of the container and having at least one open end to allow the sleeve to be displaced relative the container while the sleeve remains connected to the container.

2. A light-protective container assembly in accordance with claim 1, wherein the container is a flexible intravenous supply bag having a port structure at one end, the sleeve being configured to extend over the port structure.

3. A light-protective container assembly in accordance with claim 2 further comprising an overwrap element to enclose temporarily the container with the sleeve connected thereto.

4. A light-protective container assembly in accordance with claim 3, wherein the overwrap element has a translucent window defined therein.

5. A light-protective container assembly in accordance with claim 1, wherein the container has at least one passageway defined therethrough, the passageway being isolated from the reservoir; and the sleeve has a first portion and a second portion, the first portion attached to the second portion through the passageway to connect indirectly the sleeve to the container.

6. A light-protective container assembly in accordance with claim 5, wherein the first portion and the second portion are attached together by a heat stake.

7. A light-protective container assembly in accordance with claim 5, wherein the first portion and the second portion are attached together by a fastener.

8. A light-protective container assembly in accordance with claim 5, wherein the container includes a mounting structure to receive a support structure, at least one of the first portion and the second portion of the sleeve having a corresponding opening therethrough to allow access to the mounting structure.

9. A light-protective container assembly in accordance with claim 5, wherein the first portion of the sleeve is a first side wall having opposite lateral edge portions, and the second portion of the sleeve is a second side wail having opposite lateral edge portions, the lateral edge portions of the first side wall being integral with the lateral edge portion of the second side wall to define a tubular structure.

10. A light-protective container assembly in accordance with claim 1, wherein the identified range of wavelengths substantially prevented from transmission by the sleeve is between about 290 nanometers to about 450 nanometers.

11. A light-protective container assembly for a light-sensitive fluid, the assembly comprising:

a translucent container defining an inner reservoir to contain the fluid, the container having at least one passageway defined therethrough, the passageway being isolated from the reservoir;

a flexible sleeve connected to the container, the sleeve being made of a material capable of substantially preventing the transmission of an identified range of wavelengths of the electromagnetic spectrum, the sleeve being configured to substantially cover the reservoir of the container, the sleeve having a first portion and a second portion, the first portion attached to the second portion through the passageway to connect indirectly the sleeve to the container;

wherein the container includes a mounting structure to receive a support structure, at least one of the first portion and the second portion of the sleeve having a corresponding opening therethrough to allow access to the mounting structure.

12. A light-protective container assembly for a light sensitive fluid, the assembly comprising:

a translucent container defining an inner reservoir to contain a fluid, the container having a mounting structure to receive a support structure; and a flexible sleeve connected to the container, the sleeve being made of a material capable of substantially preventing the transmission of an identified range of wavelengths of the electromagnetic spectrum, the sleeve being configured to substantially cover the reservoir of the container and having at least one open end to allow the sleeve to be displaced relative the container, and the sleeve having an opening therethrough to allow access to the mounting structure.

* * * * *

UNITED STATES PATENT AND TRADEMARK OFFICE
CERTIFICATE OF CORRECTION

| | |
|---|---|
| PATENT NO. | : 6,613,036 B1 |
| DATED | : September 2, 2003 |
| INVENTOR(S) | : Randall M. Farmer, Marc M. Daniels and Lysander R. Garcia |

It is certified that error appears in the above-identified patent and that said Letters Patent is hereby corrected as shown below:

<u>Column 13,</u>
Line 35, after "side" delete "wail" and insert therefore -- wall --

Signed and Sealed this

Second Day of August, 2005

JON W. DUDAS
*Director of the United States Patent and Trademark Office*